United States Patent [19]

Small et al.

[11] 4,308,864
[45] Jan. 5, 1982

[54] SURGICAL EXTREMITY DRAPE

[76] Inventors: Martin H. Small, 4132 Calculus Rd., Dallas, Tex. 75234; Janeece J. Davis, 3804 Shady Creek Dr., Garland, Tex. 75042; Peggy C. Elkins, 2133 McDaniel Cir., Plano, Tex. 75075

[21] Appl. No.: 10,892

[22] Filed: Feb. 9, 1979

[51] Int. Cl.³ ............................................. A61F 13/00
[52] U.S. Cl. .............................................. 128/132 D
[58] Field of Search ............ 128/132 R, 132 D, 82 R, 128/157; 2/158, 164, 168

[56] References Cited

U.S. PATENT DOCUMENTS

| | | | |
|---|---|---|---|
| 1,735,676 | 11/1929 | Elsey | 2/162 |
| 2,126,723 | 8/1938 | Bodle | 2/168 |
| 3,934,582 | 1/1976 | Gorrie | 128/132 D |
| 3,968,792 | 7/1976 | Small | 128/165 |
| 3,989,040 | 11/1976 | Lofgren et al. | 128/132 D |
| 4,153,054 | 5/1979 | Boone | 128/132 D |

Primary Examiner—Robert W. Michell
Assistant Examiner—C. W. Shedd
Attorney, Agent, or Firm—Kenneth R. Glaser

[57] ABSTRACT

A surgical wrap or drape adapted for covering a patient's extremity during a surgical procedure. The drape is generally tubular in construction having two distinct sections; a first of stockinette material, preferably double-walled; and a second section formed from a liquid proof film. The second section is closed at one end and its opposite end is connected to one end of the stockinette section to form a continuous tubular wrap. In a preferred form, the second section includes a nonwoven fabric liner inside the liquid proof film and an elastic band bonded to the junction of the first and second sections.

4 Claims, 3 Drawing Figures

SURGICAL EXTREMITY DRAPE

BACKGROUND OF THE INVENTION

The present invention relates to surgical drapes for covering a patient's extremity during an operative procedure.

References known to the applicant and believed to be relevant to the present invention include the following U.S. Pat. Nos. 3,934,582 issued to Gorrie on Jan. 27, 1976; 3,968,792 issued to Small on July 13, 1976; and 3,989,040 issued to Lofgren, et al on Nov. 2, 1976. The Small patent, which is assigned to the assignee of the present invention, teaches various improvements in construction and use of stockinette tubular drapes which are generally made from 100% cotton woven in a seamless tubular structure. This type of tubular knit stockinette is usually woven in a stretch weave which permits the tubular structure to conform very closely to the extremity being draped and to move with the extremity without slipping relatively thereto.

The Gorrie patent discloses a tubular extremity drape having an outer layer of a fluid impervious plastic material which is intended to avoid the one basic problem occurring with the cotton stockinettes. The fabric stockinette absorbs the fluids resulting from surgery, and once it has been wet from inner to outer surface, it no longer provides a sterile barrier. The fluid impervious outer layer will obviously prevent strike-through, that is, the wetting of the drape from the inner to outer surface. But it has been found in practice that in most cases, any material which provides an effective fluid barrier is not as flexible or elastic as the stockinette material. It is highly desirable that once a drape of this type has been placed on a patient's extremity that it remain in its original position and not slide relatively to the extremity. This is due to the fact that, in general, the surgical procedure is performed through an opening, or fenestration, formed in the drape itself. This opening is desirably kept as small as possible and, as a result, any movement of the drape relative to the patient's extremity can interfere with the surgical procedure.

The Lofgren, et al patent discloses one way of insuring that a surgical extremity drape does not move relative to the extremity once it is positioned around The surgical site. The drape provided by Lofgren is similar to that taught by Gorrie in having at least an outer layer of a fluid impervious material. Instead of attempting to make the drape conform closely to the patient's extremity, to prevent slipping, Lofgren provides a pre-formed slit adjacent the open end and an adhesive strip running along both sides and the end of the slit. In this way, the drape may be positioned on the patient's extremity with the slit opening around the surgical site and the adhesive strips holding the drape in a precise position around the surgical site.

Thus, it is seen that while there is an advantage in using fluid impervious layers in surgical extremity drapes, there has also generally been found a disadvantage in not having a close conforming fit of the drape to the surgical site.

SUMMARY OF THE INVENTION

Accordingly, an object of the present invention is to provide a surgical drape having the advantages of both fabric type stockinette drapes and the fluid impervious plastic type surgical wrap.

A surgical extremity drape according to the present invention comprises two generally tubular sections; a first formed of stockinette material, and a second formed from at least a first layer of fluid impervious plastic material. The second tubular section is closed at a first end and has a second end connected to the stockinette section to form a continuous tubular wrap.

BRIEF DESCRIPTION OF THE DRAWINGS

The present invention may be better understood by reading the following detailed description of the preferred embodiment with reference to the accompanying drawings wherein.

DESCRIPTION OF THE PREFERRED EMBODIMENT

Figure 1:
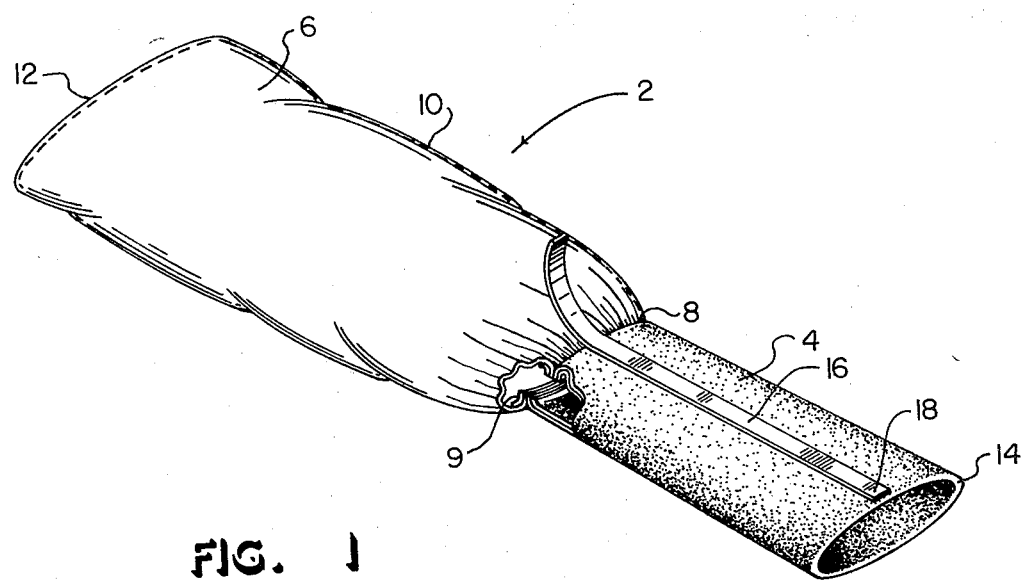
FIG. 1 is a plan view of a surgical drape according to the present invention.

With reference now to FIG. 1, there is illustrated a surgical extremity drape according to the present invention shown generally at 2. The drape 2 comprises a first section 4 and a second section 6 joined together at a seam 8. Section 4 is a fabric stockinette preferably made from a woven cotton material, although other similar stockinette materials would of course be useful. In a preferred form, section 4 has a flat folded width of about 6 inches and a length of about one foot. The embodiment having these dimensions is useful for use on a patient's leg. One of two pull straps 16 is also illustrated in FIG. 1 lying along the outside of section 4. This pull strap may be attached at an end 18 to the stockinette material, but this is not essential. The pull strap is an aid in applying the drape to a patient's extremity as will be explained more clearly below. Straps 16 are somewhat longer than section 4 so that upon folding or rolling the stockinette 4, a portion of strap 16 is left exposed.

The drape section 6, on the other hand, is formed from a layer of fluid impervious plastic material having, in the preferred embodiment, a layer of nonwoven fabric bonded to the inner surface thereof. This liner material is intended primarily for improving patient comfort and is not necessary for providing a sterile barrier. In the preferred embodiment, an antistatic polyethylene material was used for the fluid impervious layer, although other vinyl or rubber materials are known to be suitable for these purposes. In this preferred form, the nonwoven fabric actually comprised a layer of "Hyloft", a trademark of Scott Paper Co., covered by a layer of "Delnit", a trademark of Hercules, Inc.

In the preferred embodiment, intended for use on a leg, the section 6 has a flat length of about two feet and width of about one foot. The section 6 is formed from a approximately square section of material folded and joined along a seam 10 to form a tubular section which is then also joined along a seam 12 to close one end of the tubular section. In a preferred form, seams 10 and 12 are actually sewn, although various heat sealing or adhesive techniques could be used to form seams 10 and 12. In similar manner, seam 8 is also sewn to join sections 4 and 6 together. Since, with the dimensions described, the circumference of the open end of section 6 which is joined at seam 8 to one end of section 4 has twice the unstretched circumference of section 4, it can be seen that one end of section 4 tends to be stretched during the sewing operation. In a preferred form, to assure a good fit for the entire length of section 4, a narrow elastic rubber band 9 is included as part of seam 8 at the time sections 4 and 6 are sewn together. It is apparent that, since section 4 is of a fabric material, stitching is the preferred method of joining sections 4 and 6 together.

While section 4 may be a single wall stockinette section, it is preferred to use a double wall stockinette. This is conveniently done by forming section 4 from a two foot length of single wall stockinette material folded back upon itself at what then becomes the open end 14. The cut, or raw ends, of the stockinette material are then aligned and stitched together at the same time that the section 4 is joined to section 6. This construction technique provides a double wall stockinette and avoids the need for extra stitching at open end 14 to bind the raw ends.

Figure 2:
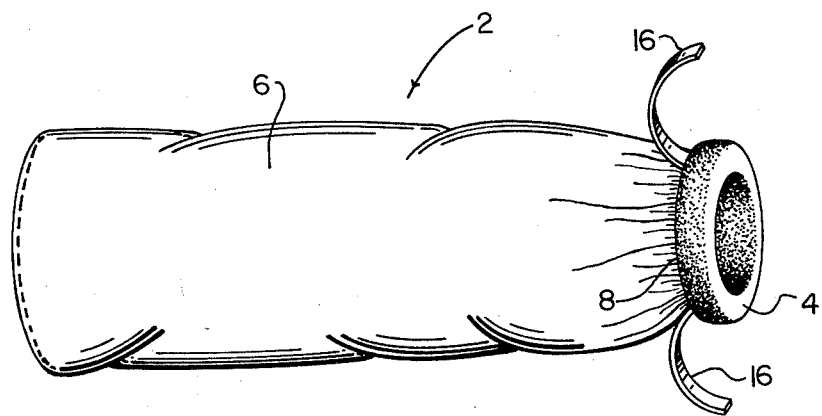
FIG. 2 is a side elevation view of the surgical drape of FIG. 1 with the stockinette section folded for application to a patient's extremity.

With reference now to FIG. 2, there is illustrated a preferred method of folding the drape of FIG. 1 in preparation for application to a patient extremity. In particular, the open end 14 of stockinette section 4 has been rolled back on itself at least to seam 8 in a toroidal, or doughnut, shape with the ends of straps 16 remaining free. This is the same technique used with the entire drape in the above referenced Small patent. It is preferred to package the thus prepared drape into a hermetically sealed envelope so that it remains sterile until use. The drape section 6 may be folded flat and then the drape may be placed in an envelope similar to that illustrated in FIG. 6 of the Small patent. It would be desirable to roll the section 6 into the doughnut shape, but this has not been practical since the plastic materials are not as elastic as the stockinette. It is contemplated that section 6 may be collapsed along its length by forming accordian type pleats. This would aid packaging, but primarily would aid application to a patient's limb.

Figure 3:
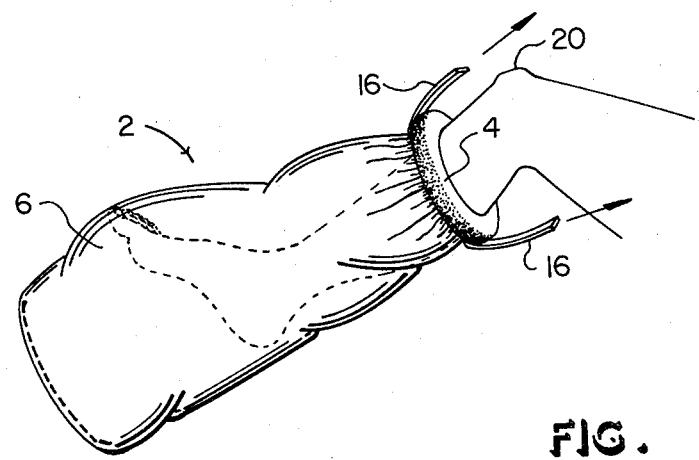
FIG. 3 is a side elevation illustration of a surgical drape according to the present invention being applied to a patient's extremity.

With reference now to FIG. 3, there is illustrated the application of the drape of FIGS. 1 and 2 to the leg of a patient. In particular, the hands of an operating room nurse may be positioned below the rolled up section 4 so the nurse may slip the drape over the patient's foot and up the leg to the desired surgical site. If, for example, the knee 20 is the surgical site, the nurse would stop drawing up the drape 2 at the position illustrated in FIG. 3. Section 4 would then be unrolled using pull straps 16 and extended over and beyond the knee 20. It is apparent that, if desired, the stockinette section 4 may be prepared in a cuff fold.

In any case, once the drape has been applied to the extremity, it is seen that the majority of the extremity below the surgery site 20 is completely covered by a fluid impervious sterile barrier. With the present invention, no particular attempt is made to make this portion of the drape conform closely to the extremity other than, in a preferred form, providing the elastic band at the top to prevent stretching of the stockinette section. The portion of the extremity near the surgical site is covered and surrounded with the stockinette section which conforms very closely to the shape of the extremity and tends to stay in position very well during the surgical operation. An opening is cut through the stockinette section to expose the surgical site in the same manner as has previously been used when the entire drape was formed from stockinette material. No particular adhesives or clamps are required to hold the drape into position. In addition, no extra effort is required for cutting through the drape since in the area of the surgical site there is no plastic or rubbery layer.

This arrangement as thus far described is believed to combine the best advantages of both the stockinette type of drape with the plastic or rubbery type drapes. In particular, the primary purpose of providing the tubular drapes for patient's extremities has been that the surgeon quite often comes in contact with the lower portion of the extremity, that is, the portion distal from the surgical site. While at times such contact would be accidental, some surgical procedures require the surgeon's manipulation of the extremity so that his contact is necessary. As noted above, the purpose of the fluid impervious layers has been to prevent the loss of sterile barrier which results when the drape becomes fluid soaked. This loss has primarily been a problem when the surgeon was required or accidentally contacted the distal portion of the extremity during the operation and, thereby, came in contact with bacteria on the patient's extremity. While the previously known fluid impervious drapes obviously avoided this problem, they also in turn created several new problems by not having the advantages of stockinette drapes in the region of the surgical site. The present invention thus provides the stockinette type close fit drape at the surgical site while also providing the fluid impervious barrier over regions of the extremity distal from the site.

While the present invention has been shown and illustrated in terms of specific apparatus and methods of use, it is apparent that various modifications may be made within the scope of the present invention as defined by the appended claims.

We claim:

1. In a surgical drape of the type covering an extremity of a patient during surgery on said extremity, the improvement wherein said drape comprises:
 a first section comprising an elongated stockinette tube open at both ends, said tube, when said drape is in place completely covering a surgical site on said extremity, being disposed around said extremity at said surgical site and closely fitted to the shape of and in engagement with said extremity to resist movement relative to said extremity at said surgical site;
 a second section completely covering the part of said extremity distal from said surgical site to form a substantially fluid impervious sterile barrier, said second section comprising an elongated tube of liquid proof film having an interior tube of fabric, and second section being closed at one end and being secured at its other end to one end of said first section;
 said first section being in a toroidal roll, said stockinette having been rolled circumferentially outward from the end opposite said second section until said roll has approached said second section; and
 at least one elongated strap extending substantially the length of said first section, positioned on the outer wall of said first section and concentrically rolled within said toroidal roll;
 whereby said elongated strap provides means to unroll said toroidally rolled first section so as to completely cover said surgical site on said extremity.

2. A surgical drape according to claim 1 wherein said stockinette is double walled and comprises a single length of single wall stockinette folded back on itself wherein the ends of the single wall stockinette are aligned and bonded to the open end of said second section.

3. A surgical drape according to claim 1 wherein said fabric tube is a layer of non-woven fabric bonded to the inner surface of said tube of flexible liquid proof film.

4. The improvement as defined in claim 1 including an elastic band secured to the junction of said first and second sections and fitted snugly around said extremity to hold said drape in position during surgery and to prevent longitudinal stretching of said first section during manipulation of said extremity.

* * * * *